United States Patent [19]

Lux

[11] 4,272,820
[45] Jun. 9, 1981

[54] METHOD OF AND DEVICE FOR REDUCING ARTEFACTS IN COMPUTED TOMOGRAPHY IMAGES

[75] Inventor: Peter Lux, Hamburg, Fed. Rep. of Germany

[73] Assignee: U.S. Philips Corporation, New York, N.Y.

[21] Appl. No.: 966,453

[22] Filed: Dec. 4, 1978

[30] Foreign Application Priority Data

Dec. 7, 1977 [DE] Fed. Rep. of Germany ....... 2754361

[51] Int. Cl.³ ............................................. G01N 23/00
[52] U.S. Cl. .................................. 364/414; 250/445 T
[58] Field of Search .................... 364/414; 250/445 T, 250/366, 362, 369

[56] References Cited

U.S. PATENT DOCUMENTS

| | | | |
|---|---|---|---|
| 4,070,707 | 1/1978 | Barber | 364/414 |
| 4,135,247 | 1/1979 | Gordon et al. | 364/414 |
| 4,144,569 | 3/1979 | Wagner | 364/414 |
| 4,149,081 | 10/1979 | Seppi | 364/414 X |

*Primary Examiner*—Edward J. Wise
*Attorney, Agent, or Firm*—Thomas A. Briody; Robert T. Mayer; Jack E. Haken

[57] ABSTRACT

A method of reducing artefacts in uncorrected images which are obtained by computer tomography and which consist of a reconstructed object image and an outer region which surrounds the object image. Image data in those elements of the outer region which are associated with a measuring path are used to derive error signals. The error signals are subtracted from the image data in elements of the uncorrected image in order to reduce artefacts which extend through the image in straight strips.

7 Claims, 3 Drawing Figures

METHOD OF AND DEVICE FOR REDUCING ARTEFACTS IN COMPUTED TOMOGRAPHY IMAGES

BACKGROUND OF THE INVENTION

The invention relates to a method of reducing artefacts in reconstruction images of a reconstructed object image and an outer region which surrounds the object image obtained by means of computer tomography. The reconstruction images are obtained by scanning a layer of an object by means of radiation which penetrates the object (for example, X-radiation) so that the object, as well as the region surrounding the object, is irradiated in a large number of directions by radiation beams which are situated in the layer. The radiation is detected by detectors which produce measuring data which characterizes the absorption of a radiation beam along a measuring path. The measuring data is used to derive image data which represent the absorption values at elements of an uncorrected reconstruction image of the irradiated layer. The image data in the reconstruction image associated with a measuring path is then used to derive error signals to correct the uncorrected reconstruction image to produce a corrected reconstruction image. The invention furthermore relates to a device for performing the method.

U.S. Pat. No. 3,936,636 describes an iterative reconstruction/correction method where the image data in reconstruction images approaches the values of the actual absorption coefficients in the successive iteration steps. To this end, a layer is irradiated in different directions by parallel radiation beams so that measuring data are determined which characterize the attenuation of radiation traversing different measuring paths. The data is converted into image data by a transformation, said image data being a first approximation of the radiation absorption coefficients of elements of a reconstruction image. The reconstruction image then consists of square elements of a matrix. By way of a transformation which is inverse to the first transformation, the image data is converted into fictitious measuring data which, if the image data is correct, corresponds to the original measuring data. A comparison between the measuring data and the fictitious measuring data produces correction data which is subsequently converted, by way of said transformation process, into correction image data which is a measure of the deviation of the image data stored by each element from the actual absorption coefficients. The modification of the image data by the correction image data results in a reduced deviation. When a given number of correction calculations is performed, the image data are close to the actual absorption coefficients.

The inverse transformation for producing the fictitious measuring data is performed so that the image data of the elements associated with the corresponding measuring path are summed along each measuring path which extends in the reconstruction image and which corresponds to the geometry of the backprojection, or along path of the radiation passing through the object.

Because the measuring paths which intersect the elements at a finite angle have a given width which is determined by the width of the detectors, the image data of each element are multiplied by a weighting factor which is determined by the distance between the center of the square element and the center line of the measuring path.

The described method enables a reduction of the deviations of the image data from measured absorption coefficients which arise during the reconstruction by means of said transformation process, the fictitious measuring data being compared with the original measuring data. However, a reduction of image artefacts caused by measuring errors such as "aliasing" and quantum noise (as described by G. Kowalski and W. Wagner in OPTICA ACTA, 1977, Vol. 24, No. 4, pages 327 to 348) cannot be achieved by means of the described method.

SUMMARY OF THE INVENTION

The invention has for its object to provide a simple correction method which reduces artefacts in which are manifested in the reconstruction image as straight strips which extend in the direction of the back-projection measuring paths. In order to reduce artefacts which cross the reconstruction image in the form of straight strips, the image data of the elements of the outside region are examined and an error signal is generated for each measuring path and is subtracted from the image data of all individual elements associated with the measuring path. The irradiation of a layer of an object is performed in a large number of directions by means of a fan-shaped radiation beam which encloses the layer and which is incident on an array of detectors. The width of the individual detectors defines the measuring paths. Alternatively, the object can be irradiated in different directions along parallel measuring paths by means of a narrow radiation beam. The subsequent transformation can be adapted to the geometries of either method of irradiation.

Depending on the position of the object during an exposure, some of the measuring paths extend through the object while others extend completely outside the object. The measuring data characterize the attenuation of the radiation at the end of each path. However, due to the measuring method used, the measuring data contain measuring errors which are caused by aliasing and/or quantum noise. Radiation which is not incident on the object and which passes only through the space surrounding the object need not be measured, because the structure of the surrounding space is known (the object is surrounded, for example, by air). The attenuation of the radiation is determined by taking into account known constant absorption coefficient of the surrounding space to determine fictitious measuring data for the corresponding measuring paths. This data does not contain the aforesaid errors.

During the reconstruction the measured measuring data as well as the fictitious measuring data from the outside space is transformed into image data which is the absorption values of elements of the reconstruction image representing the object layer. If all of the measuring data was free of errors the reconstruction image would be free of artefacts (except for artefacts caused by the transformation method used). However, the reconstruction image of the object contains artefacts due to the method of measuring measuring data containing errors. The transformation used, consists of two steps (i.e. a convolution and a back-projection) and the artefacts are not only limited to the image of the object, but are spread through the entire reconstruction image (G. Kowalski and W. Wagner in OPTICA ACTA, 1977, Vol. 24, No. 4, pages 327 to 348). Artefacts appear in the form of straight strips which extend through the object image as well as through the outside region. The directions of the artefacts corresponds to the radiation directions, defined by the measuring paths, of the back-projection used to compose the reconstruction image. The image data of the outside region however, are calculated from means of fictitious measuring data, so that artefacts can be unambiguously determined in the outside region.

In order to isolate artefacts, the elements in the outside region which are associated with each direction of the back-projection defined by a measuring path are addressed and the associated image data is examined. A method described in British Patent Specification No. 1,283,915 can be used for this purpose.

An error signal characterizing the artefacts is determined by subtracting the image data, determined by the fictitious measuring data of the error-free, known outside region from the image data calculated in the artefact along each measuring path. The error signal is subtracted from all individual image data elements of the corresponding measuring path in the region of the object image as well as in the outside region. Artefacts in the reconstruction image are thus reduced.

According to a further method in accordance with the invention, the error signals are obtained by forming a mean value of the image data of the outside region, reduced by the error-free image data which is determined by the fictitious measuring data from the outside region. An error signal is thus measured which is approximately representative of the image data associated with a measuring path. Only a comparatively small part of each measuring path need be scanned, so that the time required for correcting the reconstruction image is substantially reduced.

According to a further preferred method in accordance with the invention, the formation of the mean value is executed in two steps; the second step operates only on the image data which is below a given threshold value determined during the first step of the mean value formation.

Measuring paths in the back-projection which have a different directions may overlap in the outside region. Elements in the area of the overlapping may then include image data of whose value far exceeds the mean value of the image data of any of the overlapping measuring paths. The image data of each element of a measuring path is examined to determine whether it exceeds a given threshold value after formation of the mean value. If they exceed this threshold value, the relevant image data are not taken into account for the second formation of the mean value, so as not to disturb the error signals of individual measuring paths by such overlapping.

The invention also relates to a device for performing the method wherein (i) a data memory is provided for the storage of the measuring data as well as the image data. It is connected to an arithmetic unit for converting the measuring data into image data.

(ii) An address generator can be connected to the data memory in order to select addresses in the data memory. The address generator is connected to a comparator which is also connected to the data memory and to an address memory which selects addresses in the outside region of the reconstruction image. The comparator serves to compare the addresses supplied by the address generator and address memory to check whether there are error signals present in elements which are associated with the addresses of the outside region.

(iii) A mean value forming device can be connected to the data memory to determine a mean value of image data in the elements of the outside region associated with a measuring path. The mean value defines the error signal. The mean value forming device is connected to a subtraction circuit which is also connected to the data memory to subtract the error signal formed from the image data which are stored in the data memory and (which is associated with the measuring path).

In a further preferred embodiment of a device in accordance with the invention a threshold value detector is connected between the data memory and the mean value forming device. An input of which is connected to the output of the mean value forming device. The threshold value detector compares the addressed image data with a threshold value. The mean value forming device only receives image data which is below the threshold value.

An embodiment in accordance with the invention will be described in detail hereinafter with reference to the accompanying diagrammatic drawing in which:

DESCRIPTION OF AN EMBODIMENT

Figure 1:
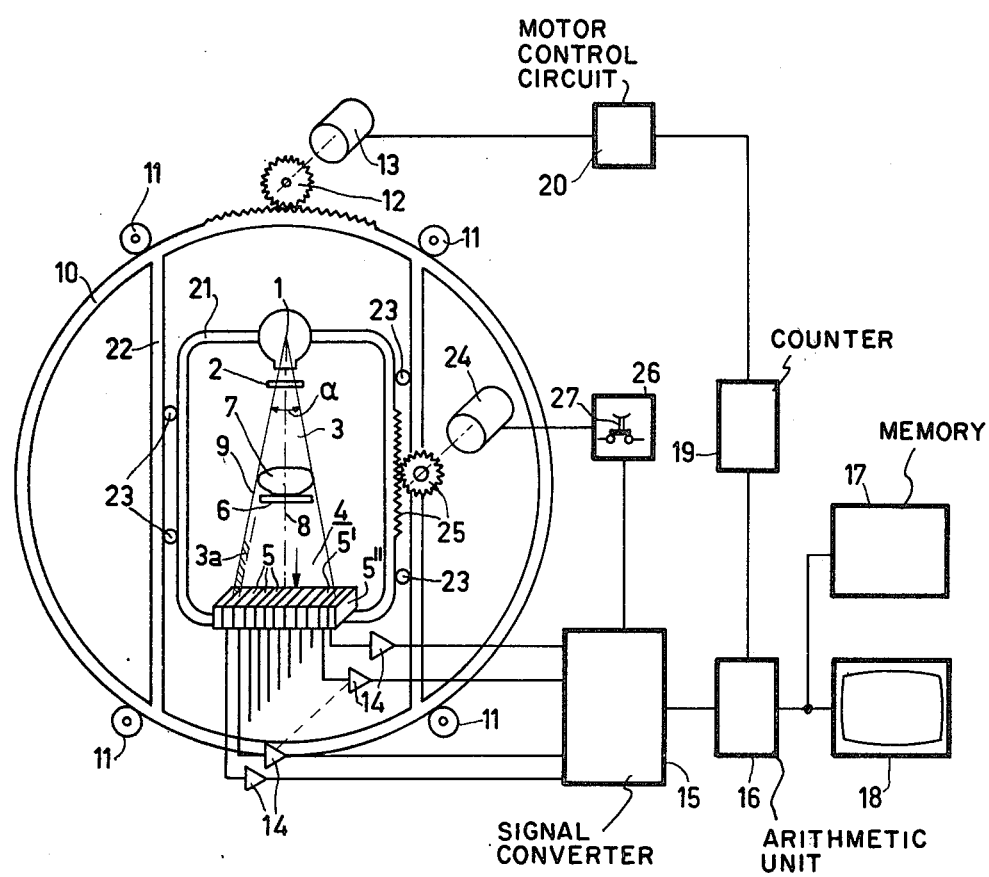
FIG. 1 shows X-ray diagnostic apparatus for examining a layer of an object.

X-ray diagnostic apparatus (as diagrammatically shown in FIG. 1) comprises a radiation source 1 which is preferably an X-ray source but which may alternatively consist of a radioactive isotope (for example, Am 241). An aperture 2 serves to collimate the radiation emitted by the radiation source 1 to form a divergent radiation beam 3 which is situated in one plane. The thickness of the radiation beam 3 perpendicular to the plane is, for example, between 3 and 25 mm, the divergence thereof in the plane is determined by the angle α. The radiation beam 3 is incident on a detector array 4 which consists of individual radiation measuring detectors 5 which define measuring beams 3a. The width of and the distance between the individual detectors 5 defines the spatial accuracy with which an object 7 positioned on an object table 6 is scanned. The detector array 4, is symmetrically situated with respect to a central ray 8 and comprises for example, 300 detectors 5. The distance between the centres of two detectors 5 amounts to a few millimeters. The detector made of can alternatively be made of an elongate gas-filled ionization chamber in which electrodes, which detect separate regions, are arranged in a row. The object 7 can be displaced, perpendicularly to the plane of the radiation beam 3, in the longitudinal direction of the axis 9 which is situated inside the object 7 and which represents the central axis of a circular frame 10, so that different layers of the object 7 can be irradiated.

The system formed by the radiation source 1 and the detector array 4 is rotatable about the axis 9, so that a layer of the object 7 can be irradiated in different directions by the radiation beam 3. The rotation of the frame 10 is guided by bearing 11 and is realized by gearing 12 which is driven by a motor 13. The rotation of the frame 10 may be continuous or intermittent, in the latter case the object 7 is flashed by the radiation source 1 after each step.

Measuring signals from the detectors 5 are amplified by amplifiers 14 and are applied to a signal converter 15 which comprises, for example, a multiplex circuit and an analog-to-digital converter. The digitized measuring data are applied, via an arithmetic unit 16, to a memory 17. The arithmetic unit 16 serves to convert the measuring data into image data which represents a reconstruction image 31 (FIG. 2) and which is again stored in the memory 17. The calculated image data can be displayed on the monitor 18. A counter 19 counts the number of measuring data applied to the arithmetic unit 16 per measuring series. As soon as the number of projection data corresponds to the number of detectors 5, a control circuit 20 is activated which briefly drives the motor 13.

It has been found that the distance between the radiation source 1 and the object 7 is preferably adaptable to the diameter of the object 7. To this end, the system formed by the radiation source 1 and the detector array 4 is mounted on a support 21 which can be displaced on bearings 23 along the guide rails 22 by means of gearing 25 which is coupled to a motor 24. A control circuit 26 can be operated, for example, by means of a manual switch 27; automatic operation of the circuit 26, however, is also possible. Prior to the start of the measurement, the measuring signals from two detectors 5' and 5" are applied, via the signal converter 15, to the control circuit 26. The support 21 is displaced so that the measuring signal from the detector 5" is maximized, while the measuring signal from the detector 5' has a lower value. The detector 5" then receives radiation which passes completely through the space surrounding the object 7, while the radiation measured by the detector 5' is attenuated by the object 7. The control circuit 26 is locked subsequently in order to keep the distance between the radiation source 1 and the axis of rotation 9 constant during the exposure. The detector 5" thus characterizes the beginning of the outside region 33, shown in FIG. 2, for the corresponding irradiation direction of the object 7. The extent of the outside region beyond the two sides of the detector array 4 is determined by the amount of measuring data to be generated, taking into account the attenuation behaviour of the space surrounding the object 7. The measuring data to be generated is calculated on the basis of the known attenuation behaviour so that it is free of errors.

Figure 2:
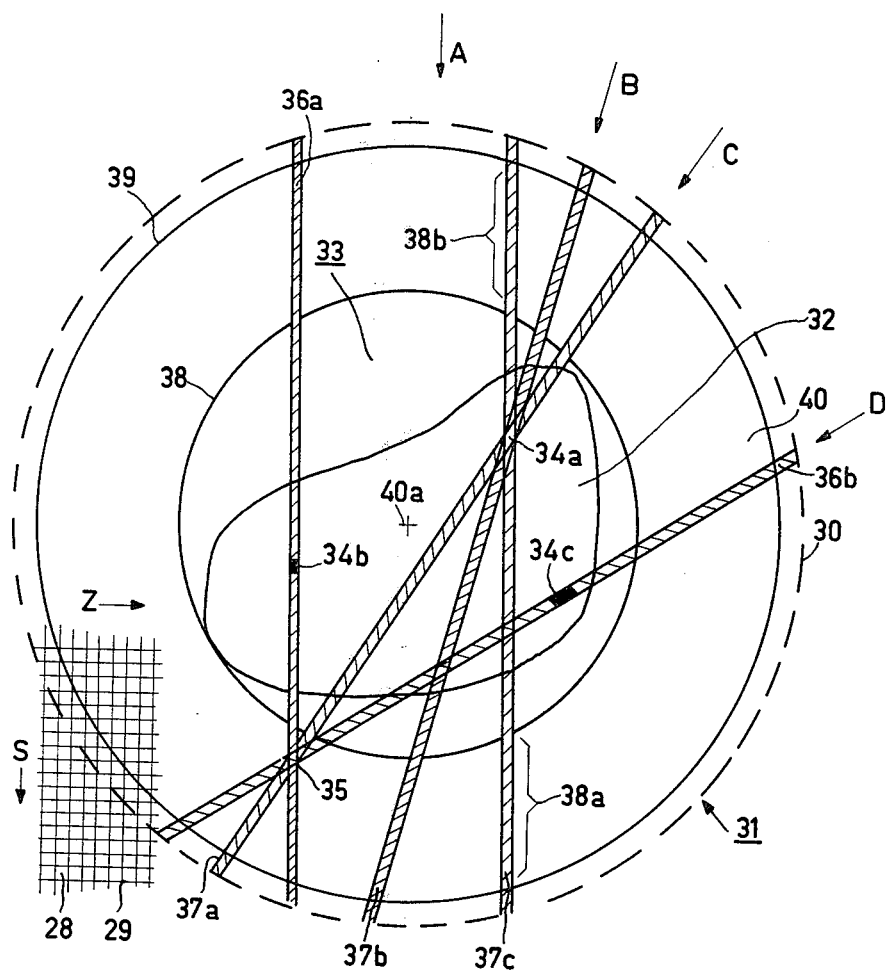
FIG. 2 illustrates the principle of the correction method.

FIG. 2 shows a matrix 29 (partly shown) which preferably consists of square elements 28 and which is composed of rows Z and columns S. This matrix 29 serves to display a reconstruction image 31 (diagrammatically shown) which is bounded by a circle 30 and which comprises a reconstructed object image 32 and an outer region 33 which bounds the object image 32. The boundary of the reconstruction image 31, represented by the circle 30, is described in known manner by rotation of the radiation beam 3 (FIG. 1) around by the object 7. Only the regions of the irradiated layer of the object 7 which are irradiated by all sub-beams in the various directions are reconstructed. The matrix 29 itself may be larger than the reconstruction image 31 bounded by the circle 30. Inside the object image 32 there are three object image structures (artefacts) 34a, b and c which are situated in straight strips 36a, 36b, 37a, 37c which extend through the object image 32 as well as through the outer region 33. In practice, the number of artefacts is substantially larger than shown in FIG. 2. Each discontinuity in absorption in the object causes a strip-shaped artefacts for each direction in which the object is irradiated. A ring which is formed by two concentric circles 38 and 39 and which extends arounds the object image 32 and completely inside the outer region 33 represents a so-called sub-region 40 having a center 40a. In reality, the circles 38 and 39 do not appear in the reconstruction image 31. In a memory yet to be described, only the addresses of the elements situated between the two circles 38 and 39 are stored. However, the radii of the circles 38 and 39 can also be stored in said memory.

After the reconstruction image 31 has been generated, the image data for elements 28 situated inside the sub-region 40 are fetched. Fetching is consecutively effected for each radiation direction A, B, C, D etc. for each measuring path extending in parallel in the region of the object image 32. The error signal for the strip 37c, situated over a measuring path in the radiation direction A, is obtained by formating the mean value of the image data of the elements situated in the path sections 38a and 38b. This error signal is subtracted, after subtraction of the value of the image data characterizing the known error-free outer region, from all image data in the strip 37c. Analogously, the image data of the strips in the other beam paths are corrected.

The strips 36a, b and 37a intersect each other at a point 35 inside the sub-region 40. This is an intersection of three strips; similarly, intersections of two, four, five and more strips will also occur. A threshold value detector is used to ensure that image data from junctions, which exceed the original mean value by a given amount, is not taken into account for calculating the second mean value in order to prevent the image data for example at point 35 of the strips 36a, b and 37a (where the artefacts of the strips 36a, b and 37a led to summation of the artefacts at the point 35) from disturbing the formation of the mean value. This amount can be preset in advance.

Figure 3:
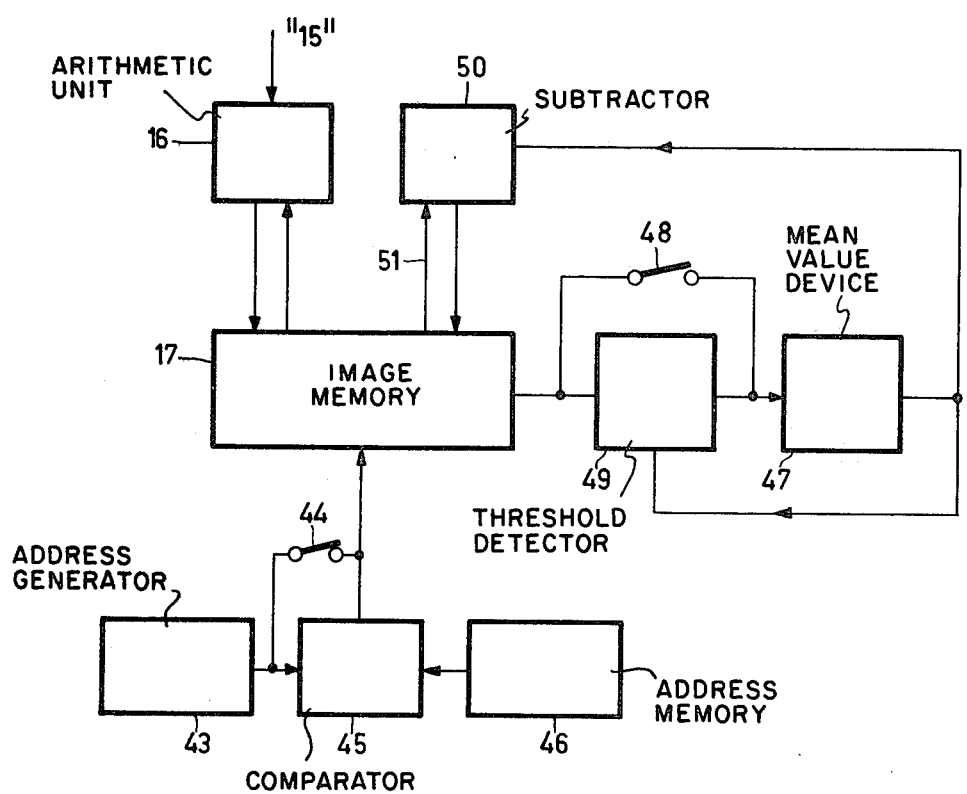
FIG. 3 shows a block diagram of a device for performing the correction method.

The method in accordance with the invention will be described in detail hereinafter with reference to the block diagram shown in FIG. 3. The measuring data originating from the signal converter 15 during the irradiation of the object are passed through an arithmetic unit 16 and are stored in a memory 17. By the described transformation, involving convolution and back-projection, the measuring data is converted, in arithmetic unit 16 into image data which is again stored in the data memory 17. The image data is accommodated in a memory matrix corresponding to the matrix 29. An address generator 43 ensures that the image data is assigned to the memory addresses in the data memory 17. A switch 44 is then closed to bridge a comparator 45. After the reconstruction image 31 has been completed in the data memory 17, the sub-region 40 (FIG. 2) is read. For this purpose, an address register 46 stores the addresses of the elements 28 which are situated inside the sub-region 40. The comparator 45 is used to compare the addresses fetched by the address generator 43 with the addresses of elements in the subregion 40 which are stored in the address memory 46. The switch 44 is then opened. Thus only image data which are associated with the addresses inside the sub-region 40 contribute to the formation of the error signal and hence to the correction of the reconstruction image. The radii of the circles 38 and 39 can also be stored in the memory 46. For each address supplied by the address generator 43, the distance from the center 40a is calculated. The comparator 45 compares the calculated distance with the radii of the circles 38 and 39, to check whether the corresponding address is situated inside the sub-region 40. This is attractive because the address memory 46 thus requires only two memory locations. In this case a small arithmetic circuit is connected between the address generator 43 and the comparator 45. Because a measuring path is examined as regards artefacts, the mean value formation device 47 forms the mean value of the image data which are associated with the measuring path and wherefrom the image data known from the fictitious measuring data from the known outside region 33 have been subtracted. The switch 48 is then closed and bridges the threshold value detector 49. Thereafter the mean value is applied to the threshold value detector 49 and forms, the threshold value from an adjustable value added to the mean value. After opening of the switch 48, the described read operation is repeated and the image data is compared in the threshold value detector 49 with the threshold value determined by the first mean value. Image data which exceed the threshold value, for example, the image data from the intersection 35, do not contribute to the second mean value formation for determining the error signal. The error signal thus obtained is subtracted, by means of the subtraction unit 50, from all individual image data which are associated with the corresponding measuring path. They are subsequently stored in the data memory 17. The same operation is performed for the image data of all further measuring paths so that a corrected reconstruction image 31 is ultimately stored in the data memory 17. For this purposes the subtraction unit 50 is connected to the data memory 17 via a connection 51 which serves to apply image data determined by the address generator 43 to the subtraction circuit 50. The switch 44 is then closed.

What is claimed is:

1. A method for producing a corrected image, with reduced artefacts, from an uncorrected image obtained by the methods of computed tomography, the uncorrected image consisting of a reconstructed object image and an outer region which surrounds the object image, comprising the steps of:
   scanning a layer of an object with radiation which penetrates the object so that the object, as well as a region surrounding the object, is irradiated in a large number of directions by radiation beams situated in the layer;
   detecting the radiation to produce measuring data which characterizes the absorption of each radiation beam along corresponding measuring paths;
   deriving image data, which represents the absorption in elements of the uncorrected image, from the measuring data; and subsequently
   reducing artefacts which cross the uncorrected reconstruction image in the form of straight strips by:
   deriving error signals from data elements in the outer region which lie along each measuring path and
   subtracting the error signals from each individual element of the uncorrected image associated with that measuring pair.

2. A method as claimed in claim 1 wherein the error signals are derived by:
   forming an error-free image of the outer region from fictious measuring data;
   subtracting elements of the error-free image from elements of the uncorrected image of the outer region; and
   forming the mean value of the results of the subtraction.

3. A method as claimed in claim 2 wherein all data elements in the outer region are processed to form a first mean value and further comprising the steps of:
   determining a threshold value from the first mean value; and
   forming a second mean value by utilizing only data from elements in the outer region which exceed the threshold.

4. A method as claimed in claim 1, 2 or 3 wherein the error signal is formed from elements in a circular subregion of the outer region.

5. A device for performing the method claimed in claim 1, 2 or 3 comprising:
   arithmetic unit means which function to convert the measuring data into image data;
   a data memory connected to the arithmetic unit means which function to store the measuring data and the image data;
   address generator means connected to the data memory which function to select addresses in the data memory;
   an address memory;
   comparator means, connected to the address generator means, the data memory, and the address memory, which function to generate addresses in the outer region of the uncorrected image and to compare the addresses supplied by the address generator means and by the address memory to determine whether or not error signals are present in elements which are identified by addresses in the outer region which are stored in the address memory;
   mean value forming means connected to the data memory which function to determine a mean value of image data in elements in the outer region which are associated with a measuring path, the mean value being the error signal; and
   subtraction circuit means, connected to the mean value forming means and to the data memory, which function to subtract the error signal from image data stored in the data memory which is associated with the measuring path.

6. A device as claimed in claim 5 further comprising threshold value detector means, connected to receive signals from the data memory, which function to compare addressed image data with a threshold value and to supply to the mean value forming means only that image data which is less than a threshold value.

7. A device as claimed in claim 5 wherein the connection between the data memory and the address generator means includes a first switch which bridges the comparator means and wherein the connection between the data memory and the mean value forming means includes a second switch connected to bridge the comparator means.

* * * * *